United States Patent [19]

Battistini et al.

[11] Patent Number: 5,302,588
[45] Date of Patent: Apr. 12, 1994

[54] CRYSTALLINE (5R,6S)-2-CARBAMOYLOXYMETHYL-6-[(1R)-HYDROXYETHYL]-2-PENEM-CARBOXYLIC ACID AND ITS PHARMACEUTICAL FORMULATION

[75] Inventors: Carlo Battistini, Milan; Roberto Bianchini, Bergamo; Stefano del Nero, Milan; Pierluigi Griggi, Monza; Sergio Vioglio, Cusano Milanino, all of Italy

[73] Assignee: Farmitalia Carlo Erba, Milan, Italy

[21] Appl. No.: 899,057

[22] Filed: Jun. 16, 1992

Related U.S. Application Data

[63] Continuation of Ser. No. 469,586, May 1, 1990, abandoned.

[30] Foreign Application Priority Data

Aug. 8, 1988 [GB] United Kingdom ............... 8818789

[51] Int. Cl.$^5$ ................. C07D 499/00; A61K 31/425
[52] U.S. Cl. .................................... 514/192; 540/310
[58] Field of Search ............... 540/222, 310; 514/192, 514/195

[56] References Cited

U.S. PATENT DOCUMENTS 4,508,649 4/1985 Alpegiani et al. ........... 260/265.2 R
4,761,408 8/1988 Schneider ........................... 514/192

*Primary Examiner*—Nicholas S. Rizzo
*Attorney, Agent, or Firm*—Oblon, Spivak, McClelland, Maier & Neustadt

[57] ABSTRACT

A crystalline form of (5R,6S)-2-carbamoyloxymethyl-6-[(1R)-hydroxyethyl]-2-penem-3-carboxylic acid incorporates two molecules of water per molecule of the acid and is useful as an antibacterial agent.

6 Claims, No Drawings

CRYSTALLINE (5R,6S)-2-CARBAMOYLOXYMETHYL-6-[(1R)-HYDROXYETHYL]-2-PENEM-CARBOXYLIC ACID AND ITS PHARMACEUTICAL FORMULATION

This application is a continuation of application Ser. No. 07/469,586, filed on May 1, 1990, now abandoned.

This invention relates to penem acids, to their preparation and to pharmaceutical formulations containing them.

The invention provides a crystalline form of (5R,6S)-2-carbamoyloxymethyl-6-[(1R)-hydroxyethyl]-2-penem-3-carboxylic acid of the formula (I) incorporating two molecules of water per molecule of the acid.

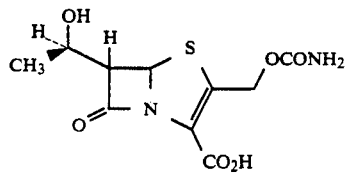

(I)

This crystalline penem acid exhibits highly desirable physical stability and solid state chemical stability and reduced hygroscopicity. These properties are unexpected and superior to those of the corresponding amorphous or freezedried sodium (5R,6S)-2-carbamoyloxymethyl-6-[(1R)-hydroxyethyl]-2-penem-3-carboxylate. That penem is useful as a broad spectrum antibacterial as described and claimed in U.S. Pat. No. 4,482,565 and U.S. Pat. No. 4,508,649. For pharmaceutical use, it is much easier to make up suitable dosage forms using a crystalline compound as opposed to an amorphous or freezedried form thereof.

The stable crystalline form of (SR,6S)-2-carbamoyloxymethyl-6-[(1R)-hydroxyethyl]-2-penem-3-carboxylic acid (FCE 22101) incorporates two molecules of water per molecule of the penem acid and has the following physics-chemical characteristics:

(a) Melting point (DSC): melting begins at 83°–85° C. (dec.) (from water-acetone)

(b) Specific rotation: $[\alpha]_D^{20} = +148°$ C. (c=0.1, 95% ethanol) $+143°$ C. (c=0.1, acetone)

(c) For $^3H$ NMR spectrum recorded at 200 MHz in DMSO-$d_6$ solution, the attributions of the main signals are as follows:

| δ (ppm) | Multiplicity | J (Hz) | Attribution |
|---|---|---|---|
| 1.13 | doublet | 6.2 | $\underline{C}H_3$—CH |
| 3.72 | double doublet | 1.6, 6.1 | $\underline{H\text{-}6}$ |
| 3.95 | double quartet | 6.1, 6.2 | $CH_3$—$\underline{C}\underline{H}$ |
| 4.0–5.5 | broad signal | — | $\underline{COOH}$ |
| 4.98, 5.20 | two doublets | 15.2 | $\underline{C}H_2OCONH_2$ |
| 5.57 | doublet | 1.6 | $\underline{H\text{-}5}$ |
| 6.60 | broad signal | — | $OCO\underline{N}H_2$ |

(d) IR spectrum recorded in KBr pellet, shows the following main absorptions

| Frequency (cm$^{-1}$) | Vibration | Attribution |
|---|---|---|
| 3700 2300 | Stretching | O—H and $NH_2$ |
| 1750 | " | β-lactam C=O |
| 1730 | " | urethane C=O |
| 1680 | " | carboxylic acid C=O |

The band at 1750 cm$^{-1}$ is highly characteristic of a β-lactam ring.

(e) UV spectrum, recorded in 95% ethanol solution, shows the following maxima:

| ν (nm) | $E_{1\,cm}^{1\%}$ |
|---|---|
| 254 | 102 |
| 316 | 209 |

(f) Solubility: the substance is soluble in acetone and methanol and very slightly soluble in water and ethyl acetate.

(g) Stability:

TABLE I

| | Stability at 20° C. as strength (%) | |
|---|---|---|
| | 3 months | 1 year |
| FCE 22101 sodium salt | 96.5 | 88.2 |
| FCE 22101 acid.$2H_2O$ | 99.4 | 93.7 |

Table I shows that the crystalline penem acid of the present invention exhibits a greater chemical stability over that of the prior art sodium salt. There is a greater difference between the data for the penem sodium salt than between that for the penem acid with two water molecules.

The present invention further provides a process for preparing crystalline (5R,6S)-2-carbamoyloxymethyl-6-[(1R)-hydroxyethyl]-2-penem-3-carboxylic acid incorporating two molecules of water per molecule of the penem acid, which process comprises:

(a) treating with an acid or an acidic resin a solution containing sodium (5R,6S)-2-carbamoyloxymethyl-6-[(1R)-hydroxyethyl]-2-penem-3-carboxylate, (b) removing impurities or residues optionally present, and (c) recovering the resultant crystalline form of the penem acid.

The acidic resin should be a cation-exchange resin in H$^+$ form. In particular the preparation of the crystalline penem acid may be performed by the following methods:

METHOD A

A batch of the penem sodium salt is suspended in a polar non-aqueous solvent together with a sufficient amount of a strong cation-exchange resin (preferably of the macroreticular type). During stirring, the almost insoluble penem sodium salt exchanges its sodium ions for hydrogen ions with dissolution of the resulting free acid form of the penem acid in the medium. The resin is separated by filtration and can be regenerated. The filtrate is diluted 1:1 with water. Treatment with active charcoal provides decontamination from coloured impurities.

Removal of the polar non-aqueous solvent (by vacuum evaporation) from the filtered solution and cooling lead to crystallization of the final product with high purity. The product can be further purified by repeating successive crystallization processes. The crystalline product is dried at room temperature (or below) under vacuum (e.g. 133–267 Pa(1–2 mm Hg)) and in the presence of a drying agent such as phosphoric anhydride.

Preferred polar non-aqueous solvents are acetone, acetonitrile, dioxane, tetrahydrofuran and ethanol. Preferred cation-exchange resins are: Dowex 50W, Amberlist 15, Amberlist XN-1010 and Amberlite 200, all in H+ form.

METHOD B

Alternatively the penem sodium salt is passed through a column packed with a gel-type strong cation-exchange resin (like Amberlite IR 120, in H+ form), eluting with acetone-water. Fractions containing the product are treated with charcoal, filtered, concentrated and cooled to 0°–5° C. until complete precipitation of the crystalline penem acid has been achieved.

METHOD C

Another method consists in dissolving the penem sodium salt in water and adding an aqueous solution of a strong acid (like sulfuric acid). The penem acid precipitates as a powder. It is filtered and dried under vacuum at room temperature until the water content reaches 10–12%, which is equivalent to two molecules of water.

The crystalline penem acid is useful as an antibacterial agent. It is typically administered parenterally, for example, intramuscularly, intravenously, subcutaneously or intraperitoneally. A therapeutically effective amount is administered to a host suffering from a bacterial infection. Depending on the type of infection and the condition of the individual infected, daily parenteral doses of from approximately 100 mg to approximately 5 g of active ingredient are used to treat warm-blooded animals, including humans, weighing about 70 kg. The preferred dosage is from approximately 500 mg to approximately 2 g.

The present invention also provides a pharmaceutical composition comprising the crystalline form of (5R,6S)-2-carbamoyloxymethyl-6-[(1R)-hydroxyethyl]-2-penem-3-carboxylic acid and a pharmaceutically acceptable carrier or diluent. The invention further provides a pharmaceutical composition comprising the crystalline form of (5R,6S)-2-carbamoyloxymethyl-6-[(1R)-hydroxyethyl]-2-penem-3-carboxylic acid and a weak base which may also comprise a pharmaceutically acceptable carrier or diluent.

Because of its increased stability, the crystalline (5R,6S)-2-carbamoyloxymethyl-6-[(1R)-hydroxyethyl]-2-penem-3-carboxylic acid with two molecules of water is particularly well suited for use as a pharmaceutical agent. Since the compound is administered parenterally, the medicament can be marketed as a powder for reconstitution to be mixed with sterile water prior to injection. The shelf-life of the FCE 22101 acid/$2H_2O$, because of its enhanced stability, is greater than that of the penem sodium salt, thereby allowing more prolonged storage prior to reconstitution, without significant material decomposition. This is a meaningful advantage of the crystalline FCE 22101 acid/$2H_2O$ when utilized commercially.

Although the powder for reconstitution could theoretically contain only the crystalline FCE 22101 acid/$2H_2O$, it preferably is a dry mixture of the compound with a weak base, typically in a molar ratio 1:1, so that upon reconstitution the resulting composition represents a pure solution having a pH in the desired range of about 4.5 to about 8.0.

Suitable weak bases to be used may be organic or inorganic, like basic aminoacids or carbonates. The preferred organic base is arginine, the preferred inorganic base is sodium carbonate. In chemical stability experiments, the sterile dry blend of the crystalline FCE 22101 acid/$2H_2O$ and arginine shows a good solid state chemical stability also at the storage temperature of 30° C. and 35° C., as shown in the following Table II. The Table reports the percent amount of related substances measured by a HPLC validated method after storage of the dosage forms for 3 and 6 months at different temperatures.

In all events, the pharmaceutical composition comprising the crystalline FCE 22101 acid/$2H_2O$ and arginine, which may contain another physiologically acceptable excipient, is considerably more stable that the lyophilized sodium penem carboxylate, previously employed in the clinical use (A. M. Lovering, D. A. Lewis, L. O. White, C. McMullin, K. R. Routh, A. P. McGowan, D. S. Reeves, "Human Pharmacokinetics of the New Penem FCE 22101", 27th Interscience Conference on Antimicrobial Agents and Chemotherapy, New York, 4–7 October 1987).

In fact, as regards the percent amount of the related substances measured by HPLC after storage at different temperatures, the sterile dry blend of FCE 22101 acid/$2H_2O$ and arginine shows a general trend upwards, closely connected with the temperature, but kept to a minimum also after 12 months at 25° C., as evidenced in the following Table III. On the contrary, the lyophilized sodium penem carboxylate exhibits a 2–3 times higher amount of the related substances at all the storage temperatures, showing an unsatisfactory shelf-life as compared to extended shelf-life times generally mandated by the health authorities.

TABLE II

Chemical stability of the crystalline FCE 22101 acid/$2H_2O$ and its dry blends with weak bases (molar ratio 1:1)
% of related substances measured by HPLC

| | | Product | | |
|---|---|---|---|---|
| Time | T | FCE 22101 acid/$H_2O$ | FCE 22101 acid/$2H_2O$ arginine dry blend | FCE 22101 acid/$2H_2O$:$Na_2CO_3$ dry blend |
| 3 months | 25° C. | 0.9 | 1.0 | 1.0 |
| | 30° C. | 1.3 | 1.9 | 1.8 |
| | 35° C. | melted | 3.1 | melted |
| 6 months | 4° C. | 0.2 | 0.3 | 0.4 |
| | 25° C. | 0.8 | 0.8 | 0.8 |
| | 30° C. | melted | 4.2 | melted |

TABLE III

Chemical stability comparison of the crystalline FCE 22101 acid/$2H_2O$: arginine dry blend (1:1 molar ratio) and lyophilized sodium penem carboxylate % related substances measured by HPLC after 12 months at:

| Dosage form | Batch No. | 4° C. | 15° C. | 25° C. |
|---|---|---|---|---|
| lyophilized | P225/23 | 3.2 | — | 10.7 |
| sodium penem | P225/34 | 3.5 | 4.7 | 7.7 |

TABLE III-continued

Chemical stability comparison of the crystalline FCE 22101 acid/2H₂O: arginine dry blend (1:1 molar ratio) and lyophilized sodium penem carboxylate

| Dosage form | Batch No. | % related substances measured by HPLC after 12 months at: | | |
|---|---|---|---|---|
| | | 4° C. | 15° C. | 25° C. |
| carboxylate | P225/38 | 2.6 | 3.7 | 7.5 |
| Dry blend | P225/19 | 0.7 | — | 1.4 |
| FCE 22101 | P225/36A | 1.4 | 2.1 | 3.6 |
| acid/2H₂O and arginine | P225/37A | 1.1 | 1.5 | 2.7 |

The pharmaceutical compositions may be in the form of a sterile injectable aqueous or oleagenous suspension. This suspension may be formulated according to the known art using suitable dispensing or wetting agents and suspending agents. Suitable suspending agents are, for example sodium carboxymethylcellulose, methylcellulose, hydroxypropylmethylcellulose, sodium alginate, polyvinylpyrrolidone, gum tragacanth and gum acacia.

Suitable dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan mooleate.

The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectable formulations.

The following Examples illustrate the invention.

EXAMPLE 1

Starting from sodium (5R,6S)-2-carbamoyloxymethyl-6-[(1R)-hydroxyethyl]-2-penem-3-carboxylate having a 86.7% purity (determined by HPLC), 5 g of this material was added to a stirred suspension of 15 g of Dowex 50W-X8 (H+ form) in 50 ml of acetone. After complete dissolution of the penem sodium salt, the solution was filtered and the resin washed with about 5 ml of acetone. The filtrate was diluted with 50 ml of deionized water. The resulting solution was decolourized by treatment with 10 g of activated charcoal at room temperature for 1 hour under stirring and then filtered through Celite.

Removal of acetone at reduced pressure and cooling of the aqueous solution gave rise to crystallization of FCE 22101 free acid. The crystalline precipitate was filtered and washed three times with 5 ml of cold deionized water. The same crystallization from acetone-water was repeated twice. Finally the product was dried under vacuum (133–267 Pa (1–2 mm Hg)) at room temperature for 48 hours in the presence of phosphoric anhydride. The process afforded the crystalline penem free acid FCE 22101 with a purity > 99.5% in HPLC (at 210 mm) and 60% overall yield.

EXAMPLE 2

Preparation of Solutions for Intramuscular and Intravenous Injections

A sample of about 1.125 kg of the sterile crystalline FCE 22101 acid/2H₂O and about 620 g of sterile L-Arginine were placed in a mechanical blender, operating in a sterile room. Processing time was optimized to give a homogeneous blend. The blend was sub-divided and the proper amount dispensed into vials and sealed to maintain sterility. To prepare an injectable solution, about 880 mg of the blend prepared by this procedure was dissolved in 1.5 ml (i.m.) or 10.0 ml (i.v.) of sterile water for injection.

We claim:

1. A crystalline form of (5R,6S)-2-carbamoyloxymethyl-6-[(1R)-hydroxyethyl]-2-penem-3-carboxylic acid incorporating two molecules of water per molecule of the said acid.

2. A pharmaceutical composition comprising the crystalline form of (5R,6S)-2-carbamoyloxymethyl-6-[(1R)-hydroxyethyl]-2-penem-3-carboxylic acid defined in claim 1 and a pharmaceutically acceptable carrier or diluent.

3. A pharmaceutical composition comprising the crystalline form of (5R,6S)-2-carbamoyloxymethyl-6-[(1R)-hydroxyethyl]-2-penem-3-carboxylic acid defined in claim 1 and a weak base.

4. A pharmaceutical composition according to claim 3 in which the weak base is arginine.

5. A pharmaceutical composition according to claim 3, further comprising a pharmaceutically acceptable carrier or diluent.

6. Method of treating a bacterial infection which comprises administering to a host suffering from such infection a therapeutically effective amount of the crystalline form of (5R,6S)-2-carbamoyloxymethyl-6-[(1R)-hydroxyethyl]-2-penem-3-carboxylic acid defined in claim 1.

* * * * *

UNITED STATES PATENT AND TRADEMARK OFFICE
CERTIFICATE OF CORRECTION

PATENT NO. : 5,302,588
DATED : April 12, 1994
INVENTOR(S) : Carlo BATTISTINI, et al.

It is certified that error appears in the above-indentified patent and that said Letters Patent is hereby corrected as shown below:

On the title page, Item [63], the PCT information has been omitted and should read as follows:

--Continuation of Ser. No. 469,586, May 1, 1990, filed as PCT/EP89/00924, Aug. 4, 1989, abandoned.--

Also, on the title page, Item [75], the 1st inventor's city should read as follows:

--Novate Milanese--

Signed and Sealed this

Ninth Day of August, 1994

Attest:

BRUCE LEHMAN

Attesting Officer    Commissioner of Patents and Trademarks